United States Patent
Berthon-Jones et al.

(10) Patent No.: US 7,089,937 B2
(45) Date of Patent: *Aug. 15, 2006

(54) DETERMINING SUITABLE VENTILATOR SETTINGS FOR PATIENTS WITH ALVEOLAR HYPOVENTILATION DURING SLEEP

(75) Inventors: Michael Berthon-Jones, Leonay (AU); Peter Bateman, West Pennant Hills (AU); David Bassin, Coogee (AU); Gordon Malouf, Gymea Bay (AU)

(73) Assignee: ResMed Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/005,770

(22) Filed: Dec. 7, 2004

(65) Prior Publication Data

US 2005/0133032 A1  Jun. 23, 2005

Related U.S. Application Data

(63) Continuation of application No. 10/683,239, filed on Oct. 10, 2003, now Pat. No. 6,845,773, which is a continuation of application No. 09/799,260, filed on Mar. 5, 2001, now Pat. No. 6,644,312.

(60) Provisional application No. 60/187,565, filed on Mar. 7, 2000.

(51) Int. Cl.
*A61M 16/00* (2006.01)

(52) U.S. Cl. .......................... 128/204.23; 128/204.18; 128/204.21

(58) Field of Classification Search ........... 128/200.24, 128/204.18, 204.21, 204.23, 207.14, 207.15, 128/207.18; 600/300, 301, 323, 484, 529, 600/533, 538

See application file for complete search history.

(56) References Cited

U.S. PATENT DOCUMENTS

| | | | |
|---|---|---|---|
| 4,550,726 | A | 11/1985 | McEwen |
| 5,503,146 | A | 4/1996 | Froehlich et al. |
| 5,692,497 | A | 12/1997 | Schnitzer et al. |
| 5,752,509 | A | 5/1998 | Lachmann et al. |
| 5,865,174 | A | 2/1999 | Kloeppel |
| 5,931,160 | A | 8/1999 | Gilmore et al. |
| 5,953,713 | A | 9/1999 | Behbehani et al. |
| 5,954,050 | A | 9/1999 | Christopher |

(Continued)

FOREIGN PATENT DOCUMENTS

GB  2 077 444  12/1981

(Continued)

*Primary Examiner*—Teena Mitchell
(74) *Attorney, Agent, or Firm*—Gottlieb Rackman Reisman, PC

(57) ABSTRACT

A method and apparatus for determining suitable settings for a servo-ventilator to be used during sleep. Respiratory characteristics of a patient are measured during an awake learning period. With these measured characteristics, a target ventilation setting may be calculated by alternative methods. The calculated setting may then be used for enforcing a minimum ventilation during a treatment period where ventilatory support is provided with a servo-controlled ventilator.

20 Claims, 4 Drawing Sheets

U.S. PATENT DOCUMENTS

| | | |
|---|---|---|
| 6,041,780 A | 3/2000 | Richard et al. |
| 6,085,747 A | 7/2000 | Axe et al. |
| 6,089,105 A | 7/2000 | Ricciardelli |
| 6,099,481 A | 8/2000 | Daniels et al. |
| 6,186,142 B1 | 2/2001 | Schmidt et al. |
| 6,273,088 B1 | 8/2001 | Hillsman |
| 6,283,119 B1 | 9/2001 | Bourdon |
| 6,286,508 B1 | 9/2001 | Remmers et al. |
| 6,287,264 B1 | 9/2001 | Hoffman |
| 6,305,372 B1 | 10/2001 | Servidio |
| 6,349,724 B1 | 2/2002 | Burton et al. |
| 6,397,845 B1 | 6/2002 | Burton |
| 6,427,689 B1 | 8/2002 | Estes et al. |
| 6,450,164 B1 | 9/2002 | Banner et al. |
| 6,561,187 B1 | 5/2003 | Schmidt et al. |
| 6,571,795 B1 | 6/2003 | Bourdon |
| 6,629,527 B1 | 10/2003 | Estes et al. |
| 6,631,716 B1 | 10/2003 | Robinson et al. |
| 6,640,806 B1 | 11/2003 | Yurko |
| 6,644,312 B1 | 11/2003 | Berthon-Jones et al. |

FOREIGN PATENT DOCUMENTS

| | | |
|---|---|---|
| WO | WO 97/14462 | 4/1997 |
| WO | WO 97/28838 | 8/1997 |
| WO | WO 98/12965 | 2/1998 |
| WO | WO 01/00264 | 4/2001 |

DETERMINING SUITABLE VENTILATOR SETTINGS FOR PATIENTS WITH ALVEOLAR HYPOVENTILATION DURING SLEEP

This application is a continuation of U.S. patent application Ser. No. 10/683,239 filed Oct. 10, 2003, now U.S. Pat. No. 6,845,773 now allowed which is a continuation of Ser. No. 09/799,260, now U.S. Pat. No. 6,644,312, which claims the Mar. 7, 2000 priority filing date of U.S. Provisional Application Ser. No. 60/187,565.

FIELD OF THE INVENTION

The present invention relates to the field of ventilatory assistance, and in particular, to methods and apparatus for determining suitable ventilator settings in patients with alveolar hypoventilation during sleep, and for delivery of those settings.

BACKGROUND OF THE INVENTION

Patients with sustained alveolar hypoventilation, such as patients with central alveolar hypoventilation syndrome (Ondine's curse), defective chemoreflexes, obesity-hypoventilation syndrome, kyphoscoliosis, and neuromuscular disease, but also the large group of patients with chronic airflow limitation, can often breathe adequately while awake but hypoventilate during sleep, particularly during rapid eye movement (REM) sleep. Therefore, these patients require ventilatory assistance during sleep. In addition, some may require oxygen therapy, particularly during sleep.

However, from the clinical perspective, it is difficult to determine a correct degree of ventilatory support to ensure adequate ventilation during all sleep stages, particularly REM sleep, while avoiding excessive ventilatory support in the awake state or in non-REM sleep. Excessive support can lead to over-ventilation with vocal cord closure and, ultimately, sleep disruption. Excessive support is also uncomfortable to the awake patient. Equally difficult is selecting the correct amount of supplemental oxygen therapy. Patients need more supplemental oxygen during periods of hypoventilation than during other periods, but excessive oxygen therapy can be deleterious or expensive.

A volume cycled ventilator set at a fixed respiratory rate and set to deliver a chosen amount of ventilation may largely solve the under-ventilation problem. However, it introduces three new problems.

Firstly, it is necessary to experiment with various tidal volume settings to find settings that achieve the desired level of blood gases. A rough estimate can be made from first principles, based on the patient's weight, height, age, sex, etc. However, differences in metabolic rate, in particular, the gas exchanging efficiency of the lungs, can introduce very large errors. In current practice, expert clinical experience is required to make such an assessment, and usually the chosen target ventilation needs to be tested overnight and iteratively refined.

Secondly, such ventilators when correctly set are uncomfortable for most patients because the patient can only breathe at exactly the rate and depth set by the machine.

Thirdly, the ventilator may not be set accurately. If the ventilator is set to give slightly too much ventilation, the subject will be over-ventilated, leading to airway closure and very high airway pressures. Alternatively, if the ventilator is set to give slightly too little ventilation, the subject will feel air hunger.

The usual clinical compromise solution is to use a bilevel ventilator set to administer a fixed higher airway pressure during inspiration and another fixed lower airway pressure during expiration. The device is typically set to trigger from the expiratory pressure to the inspiratory pressure on detection of patient inspiratory airflow and to trigger back to the expiratory pressure on cessation of patient inspiratory airflow. A backup rate is provided for the case where the patient makes no effort within a given period.

This solution is a compromise for several reasons. Firstly, it is difficult to select a degree of assistance that will adequately support the patient during, for example, REM sleep, without over-ventilating the patient during non-REM sleep or while the patient is awake. We have made measurements of the degree of support that makes typical patients feel most comfortable during the daytime and found it to be much less than the degree of support that provides adequate ventilation during sleep. In many patients, the degree of support required during sleep, when delivered to the patient in the awake state, actually feels worse than no support at all. Secondly, the square pressure waveform is uncomfortable and intrusive in patients with normal lung function. Thirdly, it is necessary to empirically set the device while the patient sleeps, and it may take several iterations to find an adequate compromise. This procedure requires highly experienced staff and is very expensive.

One method of providing more comfortable ventilatory support is proportional assist ventilation. A device using this method seeks to provide a more comfortable pressure waveform that necessarily avoids over-ventilation because the patient must supply some effort, which is then amplified by the device. Unfortunately, this method will not work in the case of patients with absent or severely impaired chemoreflexes in sleep. This problem exists in people with Ondine's curse or obesity hypoventilation syndrome, or in people in whom the coupling between effort and result reduces dramatically during sleep, for example, patients with neuromuscular disease, where accessory muscle activity is completely lost during sleep. This problem also occurs in a very wide range of patients during REM sleep when there is routinely abnormal chemoreflex control, even in normal subjects.

The broad class of servo ventilators partially address the problem of the patient requiring much less support while awake than asleep. The physician specifies a target minute ventilation, and the device supplies sufficient support to deliver the specified minute ventilation on average. While the patient is awake and making large spontaneous efforts, the device will provide zero support. However, it will provide support as required during sleep. Further refinements of the servo-ventilator including the features of a smooth pressure waveform template, resistive unloading, low source impedance so that the patient can breathe more than the target ventilation if desired, and a minimum degree of support chosen to be comfortable in the awake state are taught in commonly owned International Publication No. WO 98/12965.

The above approaches all require the specification of a target ventilation, and either a respiratory rate or a backup respiratory rate. In addition, in patients requiring added supplemental oxygen, it is necessary to also specify the amount of added oxygen. Finally, using the above approaches, if the device is incorrectly calibrated, it will deliver a different minute ventilation than the one chosen.

BRIEF DESCRIPTION OF THE INVENTION

It is an objective of the present invention to permit the determination of suitable ventilator settings and supplemental oxygen flow rate, for use with a servo ventilator, by measurements and observations made on the subject during the daytime.

It is a further objective to permit the delivery of the chosen settings even in the case of incorrect calibration of the ventilator.

Further objectives, features and advantages of the invention will become apparent upon consideration of the following detailed description.

In its broadest sense, the present invention involves a method and apparatus for determining ventilator settings such as a desired target ventilation and/or respiratory rate. During a learning period, while a patient is preferably in a relaxed and awake state, respiratory or ventilation characteristics including, minute ventilation, and optionally blood gas saturation, such as arterial hemoglobin oxygen saturation, and respiratory rate, are measured by a ventilator. The measurements are then used to determine ventilator settings for use during the patient's sleep. In a preferred form, the device automatically calculates the desired target ventilation and respiratory rate during or at the end of the learning period, and saves and later applies these settings during subsequent therapy.

In one embodiment, the ventilation target is calculated as a fixed percentage of an average ventilation taken over the entire learning period. Alternatively, the ventilation target may be a fixed percentage of an average ventilation taken over a latter portion of the learning period to eliminate ventilation measurements from non-relaxed breathing efforts from an initial portion of the learning period. In a still further alternative, the ventilation target is determined from a graph of spontaneous ventilation and oxygen saturation measurements made during the learning period. In this method, the target ventilation is taken as a fixed fraction of the ventilation that on average achieves a desired arterial oxygen saturation level.

DETAILED DESCRIPTION OF THE INVENTION

Figure 1:
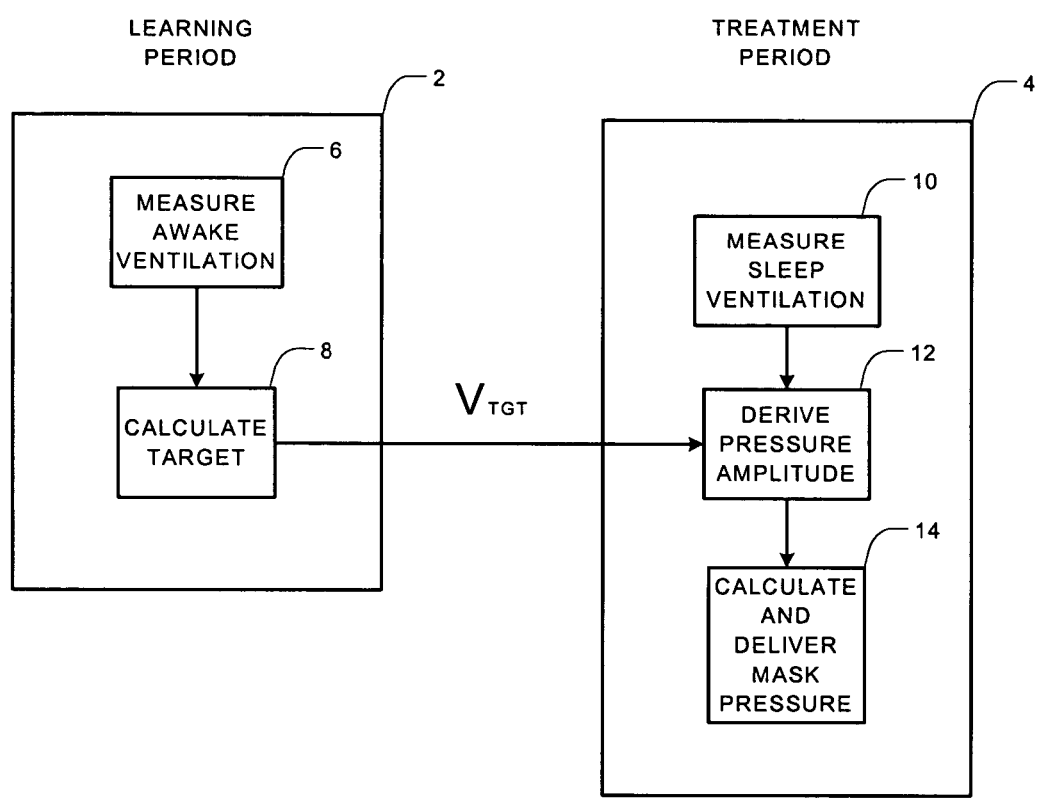
FIG. 1 shows a flow chart for an embodiment of a simple form of the invention.

Referring to FIG. 1, a method embodying the present invention generally involves a learning period 2 and a treatment period 4. During the learning period 2, a ventilator setting, such as a target ventilation $V_{TGT}$, is determined (step 8). This determination is based upon respiratory characteristics of the patient, for example, a measure of ventilation, taken while a patient is awake (step 6). The target ventilation is then used during the subsequent treatment period 4 while the patient sleeps. In a typical application, the learning period 2 is in the daytime, with the patient awake, and the treatment period 4 is at night, with the patient asleep. However, more generally, the learning period 2 is any period where the patient is quietly awake, and the treatment period 4 (or in general, periods) may also be any time of day or night, with the patient either awake or asleep in any combination.

For example, consider a learning period 2 in which a patient is quietly relaxed and awake. The patient is for preference distracted from breathing, for example, by watching television but remaining still and quiet. Typically, the learning period will be of the order of one hour's duration or longer, although shorter periods are practical. During the learning period 2, the subject breathes via a nosemask, facemask, or other suitable interface, as chosen for use during sleep, from a servo-ventilator such as the apparatus of FIG. 4. During this learning period 2, the servo-control of ventilation is disabled, and the device is set to deliver a fixed minimum degree of support (pressure modulation amplitude) $A_{MIN}$, typically 6 cm $H_2O$, chosen to make the patient feel comfortable.

Figure 2:
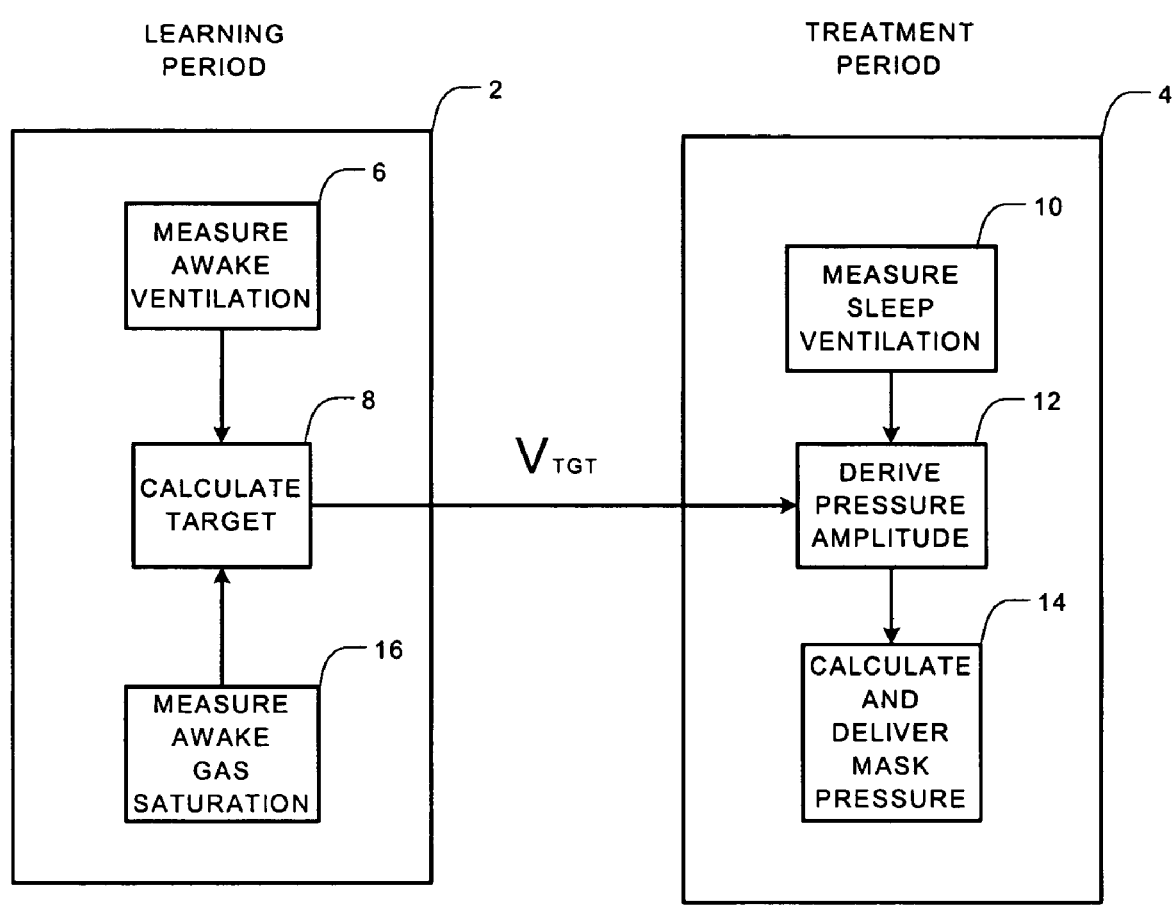
FIG. 2 shows a flow chart for an embodiment of a more elaborate form of the invention.

During this learning period, ventilation is measured (step 6). Optionally, as shown in FIG. 2, oxygen saturation levels may be measured (step 16) by an oximeter. A target ventilation for use during sleep is selected or determined (step 8) based on the ventilation measurements and optionally oxygen saturation measurements. Thus, a target ventilation may be, for example, set to be just under the known adequate measure of ventilation. If, during the learning period, the patient were completely relaxed and awake throughout the period, and unaware of breathing, then ventilation would settle to a value demonstrably adequate in the awake state, or at least substantially better than during untreated sleep, and therefore adequate for treatment during sleep.

Switching from a learning period 2 to a treatment period 4, the target ventilation is used by the ventilator to deliver ventilation. The ventilator will measure the patient's ventilation during sleep in step 10. The ventilator will then derive a pressure amplitude to maintain delivered ventilation to at least equal the target ventilation in step 12. Mask pressure is then calculated and delivered to the patient, in step 14, as a function of the pressure amplitude. The ventilator will then maintain actual ventilation to at least equal the target ventilation. Optionally, a target respiratory rate may also be set to a value determined during the learning period. For preference, this is the average respiratory rate during the last 75% of the learning period.

The first advantage of this method is that the target ventilation (and optionally the respiratory rate) is now demonstrably known to be suitable for the particular patient. The second advantage is that any errors in measurement of ventilation by the device will be cancelled out, and the device will guarantee at least the chosen fraction of the patient's spontaneous awake ventilation.

In one embodiment of the invention, the target ventilation is a target minute ventilation taken as a fixed percentage of the average minute ventilation during the entire learning period. Typically this percentage will be 90%, to allow for the fact that metabolic rate decreases slightly during sleep. In a preferred embodiment, the above calculation is made by the device itself. The principle underlying this method is that the subject has on average relatively normal arterial partial pressure of carbon dioxide while awake, the principal abnormality of ventilation being confined to sleep. Since the relationship between minute ventilation and arterial carbon dioxide is approximately linear over small departures from the mean, the average ventilation awake will ensure the average partial pressure of carbon dioxide awake.

Many subjects do indeed have elevated carbon dioxide tension in the daytime as well as at night, but if the nocturnal rise is prevented, then the subject will gradually over days reset his or her respiratory controller to a more normal set-point. It would then be appropriate to repeat the daytime learning procedure and determine a new target ventilation after about one to two weeks of therapy, to take advantage of this resetting.

It would in principle be possible to calculate a final target ventilation for use during the treatment period from a measure of the subject's awake daytime arterial partial pressure of carbon dioxide, the desired final awake daytime partial pressure of carbon dioxide, and the current target ventilation from a prior learning period. A simple calculation, ignoring changing dead space to tidal volume ratio is: Final target ventilation=current target ventilation times current awake arterial partial pressure of carbon dioxide divided by final desired awake arterial partial pressure of carbon dioxide. However, applying this final target ventilation immediately within the treatment period would lead to akalosis and vocal cord closure during sleep. This will disturb the effectiveness of therapy by inducing upper airway obstruction.

In a second and preferred embodiment, the first portion of the learning period, typically 20 minutes, is discarded because the patient is typically particularly aware of his or her ventilation as a result of commencing ventilatory therapy. Thus, the measurements from steps 6 and 16 are recorded only during a second portion, preferably lasting 40 minutes or more.

A third embodiment is useful in the case where the subject's breathing changes slowly with time by a large amount during the learning period, for example, if the subject is initially very anxious, later breathes normally, and finally falls asleep and desaturates. To address this situation, measurements of oxygen saturation are taken with an oximeter along with measurements of spontaneous ventilation. At the end of the learning period, a graph of oxygen saturation versus spontaneous ventilation is drawn. Then, using this graph, the target minute ventilation is taken as a fixed fraction (typically 90%) of the ventilation that on average achieves a desired arterial oxygen saturation.

The basis for this method is that some subjects, for example, those with obesity hypoventilation syndrome, fall asleep easily for short periods during the learning period. During these short periods, the subjects will reduce their ventilation and desaturate. Thus, it is intended that the method use only data from periods where the awake saturation is adequate.

Conversely, other patients, particularly early in the learning period, are anxious and over-ventilate. Periods where the ventilation is very high but the saturation has not importantly increased should therefore also be ignored. Because the subjects are awake during the learning period, they will tend to fidget and move about, which causes oximeter artifact. Therefore, the subjects should be made very comfortable and asked to relax and remain quiet and still as far as possible.

Preferably, the oximeter is a pulse oximeter with excellent movement artifact immunity, such as the device produced by the Masimo Corporation. However, due to patient circulation times and processing times in the oximeter, changes in saturation lag changes in ventilation by typically 20–30 seconds. Furthermore, due to the oxygen storage capacity of the lungs and blood, very short changes in ventilation (typically less than 10–40 seconds) produce little or no change in saturation. Therefore, the ventilation measurements should be delayed by the expected circulation time plus oximeter processing time (e.g., 20–30 seconds), and low-pass filtered to compensate for the low-pass filtering of the saturation by the body oxygen storage capacity (e.g., with a time constant of 10–40 seconds) in order to better relate changes in saturation to changes in ventilation.

Figure 3:
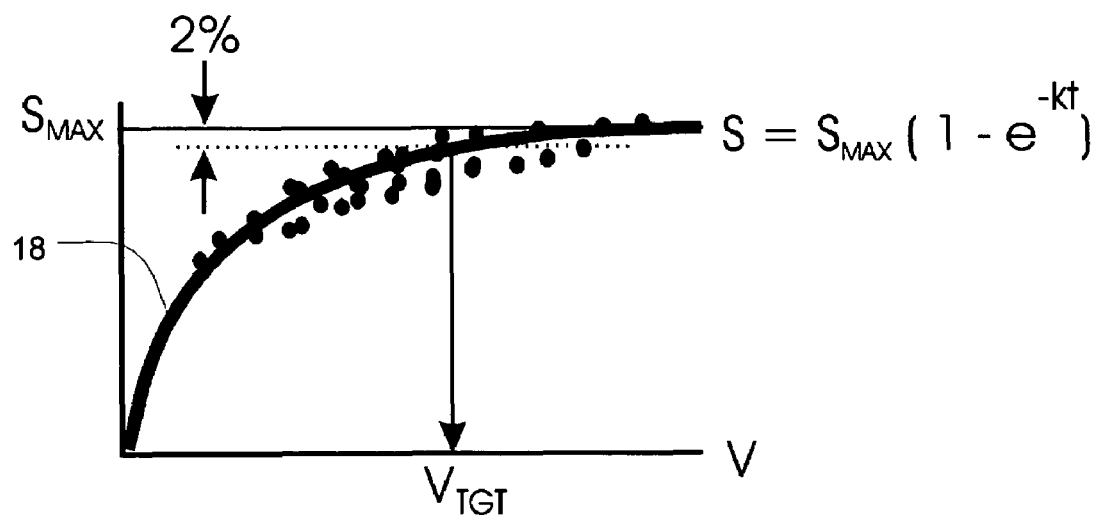
FIG. 3 shows a graph of saturation vs. ventilation with a fitted exponential curve and calculated target ventilation.

This selection of a suitable delay and time constant can be done automatically, for example, by using the method of least squares nonlinear regression to search the expected range of delay and time constants to find the combination that minimizes the scatter around the saturation vs. ventilation graph. For example, the least squares procedure can fit an exponential curve to the saturation vs. ventilation graph, such as $$S = S_{max}(1 - e^{-kv})$$

where S is the saturation, v is the ventilation, and $S_{max}$ and k are fitted constants. However, there is no particular physical significance in the use of the exponential curve. The actual shape of the saturation vs. ventilation graph is very complex, and an exponential curve is just one of a large number of curves that could be fitted. One such fitted curve 18 is represented in the graph of FIG. 3.

Typically, the desired arterial oxygen saturation will be in the range 90–95%, for example 92%, because a goal of ventilatory support is to keep the saturation above 90%, but 95% is normal during sleep. The desired level of arterial oxygen saturation can be chosen by the clinician with reference to the patient's clinical condition. Thereafter, in a preferred form, the target ventilation can be calculated automatically from the above fitted exponential equation. Alternatively, the desired oxygen saturation can be chosen by inspection of the oxygen saturation vs. ventilation graph. In general, the graph will include a quasi-plateau portion at high ventilations, where further increases in ventilation yield little further increase in saturation but risk over-ventilation and hypocapnia, and a steep portion at low ventilations, where the risk is of hypoxia and hypercapnia. A suitable desired saturation is two percent below the plateau saturation. For example, in a subject with normal lungs, the plateau will commence at 97%, and even doubling the ventilation will not increase saturation above 98%. Therefore, a suitable desired saturation would be 95%. In subjects with lung disease, the plateau will begin at a lower saturation than in normal subjects. In a preferred embodiment, the desired saturation is calculated automatically as, for example, 2% less than the constant $S_{max}$. This is illustrated in FIG. 3.

However, this least squares nonlinear regression method is not useful in the case where there are negligible slow changes in saturation because it will not be possible to fit an exponential to the saturation vs. ventilation graph. If the standard deviation of the saturation residuals about the fitted curve is not less than approximately 50% of the standard deviation about a simple average saturation, then the target ventilation should be calculated as in the second embodiment (for example, 90% of the mean ventilation during all but the first 15 minutes of the learning period).

The above procedures will yield at least a good first estimate of ventilator settings, without having to adjust the ventilator settings during the night. However, a potential problem with the embodiments described above is that the subject might stably over-ventilate or under-ventilate for the entire period of the learning session. Therefore, in some subjects, it may be desirable to confirm that the target ventilation is satisfactory by measuring arterial or arterialized capillary carbon dioxide concentration in the morning following overnight therapy, and increasing the target ventilation if the morning arterial carbon dioxide concentration is too high, or decreasing the target ventilation if the morning arterial carbon dioxide concentration is too low. Another approach to guard against the effects of sustained over or under-ventilation during the learning period is to measure arterial blood gases, particularly arterial $P_{CO_2}$, pH, and bicarbonate at the end of the learning session. In stable subjects, the pH will be in the normal range, and in subjects who over-ventilated or under-ventilated, the pH will be altered. Standard nomograms are available which would permit one to calculate the $P_{CO_2}$ that the subject would have had if they were breathing steadily. The target ventilation should then be multiplied by the ratio of the observed $P_{CO_2}$ to the estimated stable $P_{CO_2}$.

The target ventilation calculated using any of the above procedures is based on the assumption that the ventilation that is adequate in the daytime, i.e., while the patient is awake, will also be adequate at night, i.e., while the patient is sleeping, if allowance is made for a reduction in metabolic rate. As previously mentioned, clinical methods of calculating a target ventilation also attempt to allow for variations in metabolic rate, for example, by using age, height, weight, sex, skinfold thickness, etc., and gas exchange efficiency (chiefly dead space to tidal volume ratio, but also V/Q distribution, arterial-alveolar oxygen tension gradient, diffusing capacity, spirometry, clinical experience, and so forth). The present method is in principle more robust than these methods because it very directly measures the patient's actual ventilatory need. Nevertheless, it is possible to produce a final target ventilation which is a weighted average of the present method and any combination of other methods. For example, patient estimation information such as age, height, weight, sex, alveolar dead space, etc., may be used with any other known estimation method to calculate an estimated target ventilation using the other known method. Then a final target ventilation may be determined, which is a weighted average of the present method and the other known estimation method. Alternatively, the target ventilation calculated from an awake learning period may be used as one input variable to an expert system, for example, a fuzzy expert system, in which other input variables include one or more of age, height, weight, sex, severity and kind of disease, spirometry, blood gases, alveolar dead space and other lung function results.

Several of the above methods calculate a mean ventilation over a period of time. If the measurement of ventilation (as opposed to the subject's actual true ventilation) is noisy, it may be advantageous to calculate a more robust measure of central tendency, such as a trimmed mean or a median. Similar comments apply to other quantities measured, such as respiratory rate and arterial oxygen saturation measured by pulse oximetry.

Some patients require the addition of supplemental oxygen in order to maintain adequate oxygenation and saturation, even if minute ventilation is adequate. This is due to ventilation-perfusion mismatch. In such patients, the learning period may be repeated at one or more different levels of inspired oxygen, e.g., 21%, 24%, and 28%, or at one or more different levels of added oxygen, e.g., 0, 2, and 4 L/min. This will yield three different target ventilations, at three corresponding saturation levels. The physician may then choose one particular supplemental oxygen level, and the corresponding target ventilation. In general, this will be the lowest added oxygen level that permits a satisfactory saturation at a practicable target ventilation. If the ventilator is then set to deliver the target ventilation with the selected level of supplemental oxygen therapy, then the subject will still be guaranteed adequate ventilation, and the saturation will also be adequate, providing the ventilation-perfusion mismatch does not worsen significantly during sleep.

Figure 4:
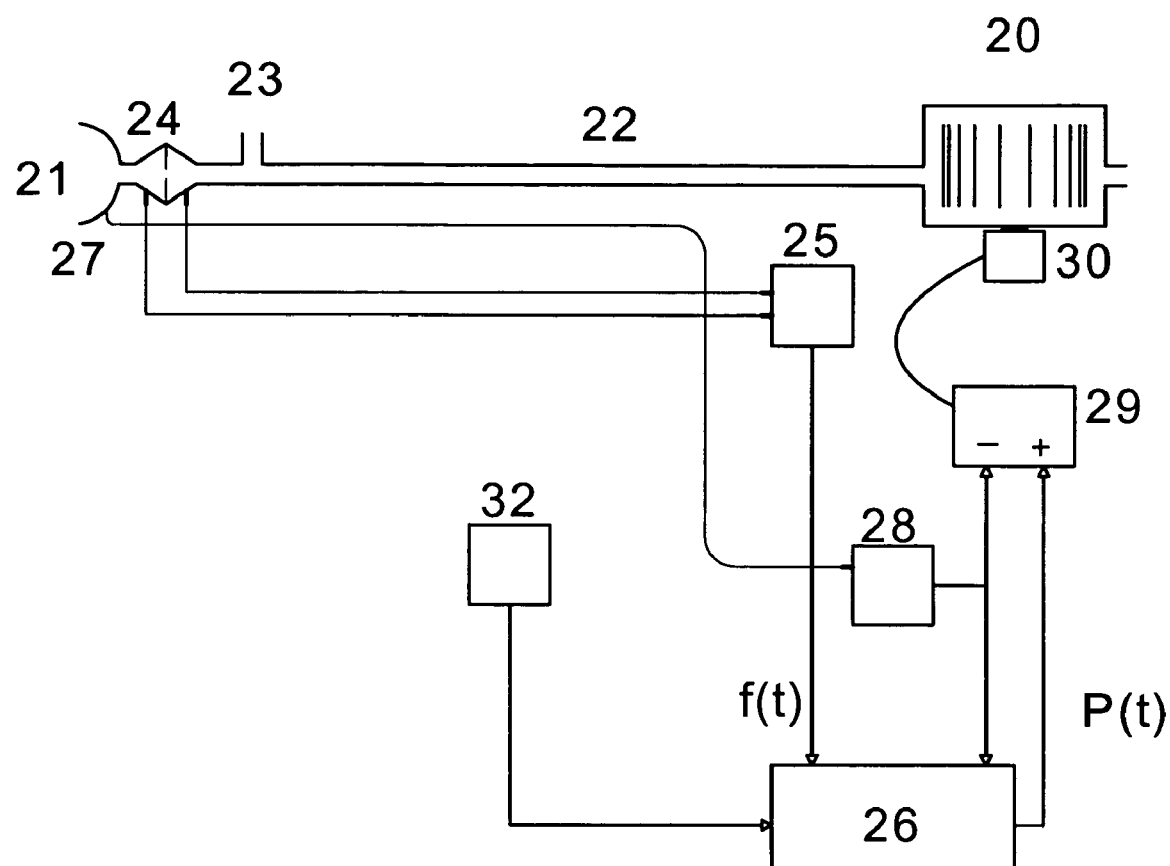
FIG. 4 depicts an illustrative apparatus for implementing the method of the invention.

A suitable apparatus for implementing these methods is shown in FIG. 4. The apparatus is described in more detail in commonly owned International Publication No. WO 98/12965 entitled "Assisted Ventilation to Match Patient Respiratory Need." (U.S. patent application Ser. No. 08/935,785, filed on Sep. 23, 1997). The foregoing application is hereby incorporated by reference. Generally, the apparatus provides breathable gas at controllable positive pressure to a patient's airway. Referring to FIG. 4, a blower 20 supplies breathable gas to a mask 21 in communication with a patient's airway via a delivery tube 22 and exhausted via an exhaust 23. Airflow at the mask 21 is measured using a pneumotachograph 24 and a differential pressure transducer 25. The mask flow signal f(t) from the transducer 25 is then sampled by a microprocessor 26. Mask pressure is measured at the port 27 using a pressure transducer 28. The pressure signal from the transducer 28 is then sampled by the microprocessor 26. The microprocessor 26 sends an instantaneous mask pressure request (i.e., desired mask pressure) signal P(t) to a servo-controller 29, which compares the pressure request signal with the actual pressure signal from the transducer 28 to control a fan motor 30. Microprocessor settings can be adjusted via a serial port (not shown).

It is to be understood that the mask could equally be replaced with a tracheotomy tube, endotracheal tube, nasal pillows, or other means of making a sealed connection between the air delivery means and the patient's airway. Moreover, as an alternative to the blower 20, the ventilator may use any source of breathable gas including air/oxygen mixtures at controllable pressure.

The microprocessor 26 accepts the mask airflow and pressure signals, and from these signals determines the instantaneous flow through any leak between the mask and patient, by any convenient method. For example, the conductance of the leak may be estimated as the instantaneous mask airflow, low-pass filtered with a time constant of 10 seconds, divided by the similarly low-pass filtered square root of the instantaneous mask pressure, and the instantaneous leakage flow may then be calculated as the conductance multiplied by the square root of the instantaneous mask pressure. Respiratory airflow is then calculated as the instantaneous mask airflow minus the instantaneous leakage flow.

Figure 5:
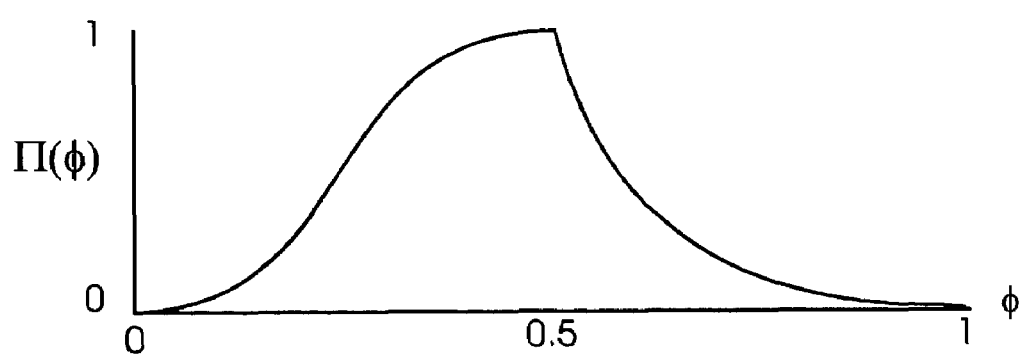
FIG. 5 depicts a smooth and comfortable ventilator waveform template function $\Pi(\Phi)$ which when multiplied by an amplitude specifies one component of the mask pressure as a function of phase.

The desired mask pressure is described by the following equation:

$$P = P_0 + Rf + A\Pi(\Phi)$$

where:

$P_0$ is a desired end expiratory pressure chosen to splint the upper and lower airways or alveoli, or to reduce cardiac preload or afterload, for example, 5 cm $H_2O$;

R may be zero, but is preferably any value less than the patient's actual airway resistance;

f is respiratory airflow, measured, for example, using a pneumotachograph in the mask, and correcting for leak, for example, as described in the commonly owned International Publication referred to above;

$\Phi$ is the phase in the patient's respiratory cycle; taken as varying between zero and 1 revolution, with zero corresponding to start of inspiration and 0.5 corresponding to start of expiration, preferably calculated using fuzzy logic;

$\Pi(\Phi)$ is a pressure waveform template, initially set to be similar to that shown in FIG. 5, for example, comprising a raised cosine followed by an exponential decay (unlike a true exponential decay, the waveform of FIG. 5 falls exactly to zero by the end of expiration, so that there is no step change at the start of the next breath); and A is a pressure modulation amplitude, for example, using clipped integral control as follows:

$$A = -G \int (0.5|f| - V_{TGT}) dt,$$

where G is a servo gain (for example, 0.3 cm $H_2O$ per L/min per second), $V_{TGT}$ is a desired target ventilation (e.g., 7.5 L/min), and the integral is clipped to lie between $A_{MIN}$ and $A_{MAX}$ (for example, 3 and 20 cm $H_2O$) chosen for comfort and safety.

To implement the learning period methods using this apparatus, the microprocessor 26 may be programmed to implement a "learn" mode and a "treat" mode. During the "learn" mode, the pressure modulation amplitude A is set to a very low value, chosen to be enough to make the patient feel comfortable while awake, but not enough to do all the work of breathing. In all subjects, an amplitude of 3 $cmH_2O$ will be satisfactory. However, the exact value is non-critical. In some subjects with very high work of breathing, larger values can be used if desired. During this learn mode, the microprocessor 26 may store ventilation data, for example, in SRAM or EEPROM, for use in calculation of the target ventilation $V_{TGT}$. Optionally, the microprocessor 16 may also store arterial hemoglobin oxygen saturation data from a pulse oximeter 32, or other similar device for this calculation. At the conclusion of this mode, the microprocessor 26 automatically calculates the target ventilation and automatically stores this target ventilation for subsequent use. During subsequent therapy, with the device in the "treat" mode, the pressure modulation amplitude is automatically adjusted in order to servo-control ventilation to equal or exceed the target ventilation determined in the "learn" mode.

While this embodiment of the invention incorporates both the learn and treat modes into a single apparatus, various simplifications are possible. For example, the device used to measure ventilation during the learning period may be different from the device used to subsequently treat the patient. In this case, the target ventilation can be calculated manually or by using analog electronics and the target ventilation can be stored and/or transferred manually to another ventilator to be used during the treatment period.

It is desirable that the device should not accidentally be delivered to the patient for unattended use unless it is certain that the device is in the "treat" mode, using settings that have been correctly determined either in the "learn" mode or as prescribed manually by a physician. Therefore, in a preferred form, a device embodying the invention has three modes, the "learn" and "treat" modes described in detail above, plus an inoperative mode in which the device will not operate. The default state as delivered is the inoperative mode. It may be placed in any of the three modes by the physician, for example, by sending commands to the microprocessor via a serial port. However, if it is inadvertently left in the "learn" mode, it will automatically revert to the "inoperative" mode on power-up.

In a preferred form, the device can be programmed to remain in "learn" mode for a specified period of time, such as 1 hour, and at the expiry of said time, the microprocessor will notify the physician, for example, via a serial port or other input/output device, of the settings determined during the learning period using any of the automatic methods described above. The physician will then be prompted to accept or edit these settings, and after acceptance or editing, the device will automatically switch to the "treat" mode at these accepted or edited settings.

For several of the disclosed methods, the ventilation quantity measured is minute ventilation and the calculated target ventilation is intended for use with a servo-ventilator with fuzzy phase detection and resistive unloading as described and illustrated in FIG. 4. However, the general method is equally applicable to a simple servo ventilator. Furthermore, if the ventilation quantity measured is tidal volume, and the calculated quantity is a target tidal volume, the controlled device can be a volume cycled ventilator.

An embodiment of the invention using the apparatus of FIG. 4 was tested in nine subjects with a wide variety of respiratory disorders, including kyphoscoliosis, neuromuscular disease, obesity-hypoventilation syndrome, and chronic airflow limitation. In this embodiment, the respiratory therapist estimated the target ventilation by eye from a graph of saturation vs. ventilation. In every case, as assessed using polysomnography, overnight oximetry, transcutaneous $PCO_2$, and morning blood gases, the subjects slept and breathed either as well as, or better than, they did on another night in which they were treated using standard bi-level therapy manually titrated by an expert respiratory therapist skilled in the art. The target ventilation was also calculated as 90% of the mean ventilation during the latter 40 minutes of each learning period. There was a 97% correlation between the target ventilation automatically calculated from the minute ventilation only, and the target ventilation estimated by-eye from the saturation vs. ventilation graphs, demonstrating that in most subjects, it is not necessary to measure saturation.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

What we claim is:

1. A method for determining at least one setting of a ventilator to be used during sleep comprising the steps of:
    measuring at least one respiratory characteristic of a patient during a learning period while the patient is awake; and
    determining at least one setting value from said at least one respiratory characteristic to be used for the operation of said ventilator during a subsequent treatment period of sleep.

2. The method of claim 1 wherein said at least one respiratory characteristic is a measure of ventilation.

3. The method of claim 2 wherein at least one setting value is a target ventilation.

4. The method of claim 3 wherein said target minute ventilation is a function of said measure of ventilation.

5. The method of claim 4 wherein said function is a fixed proportion.

6. The method of claim 5 wherein said fixed proportion is about 90%.

7. The method of claim 2 wherein another said respiratory characteristics is arterial hemoglobin oxygen saturation.

8. The method of claim 7 wherein at least one setting value is calculated from the relationship between said oxygen saturation and said measure of ventilation.

9. The method of claim 2 wherein at least one setting value is derived through a fuzzy expert system with input variables including a target ventilation derived from said measure of ventilation and patient estimation information.

10. The method of claim 9 further comprising the step of analyzing patient estimation information to determine an estimated target ventilation, wherein said setting value is a calculated weighted average of said estimated target ventilation and a second target ventilation derived from said measure of ventilation.

11. The method of claim 3 wherein said step of measuring at least one respiratory characteristic includes deriving measures of spontaneous ventilation and measures of arterial oxygen saturation.

12. The method of claim 11 wherein said step of determining a setting value includes an analysis of a graph of said measures of spontaneous ventilation and measures of arterial oxygen saturation.

13. The method of claim 12 wherein said graph includes a fitted curve derived from said measures of spontaneous ventilation and measures of arterial oxygen saturation using least squares nonlinear regression.

14. The method of claim 13 wherein said curve is an exponential function.

15. The method of claim 13 wherein said measures of spontaneous ventilation are delayed and low-pass filtered to associate changes in said arterial oxygen saturation with changes in said measures of spontaneous ventilation.

16. The method of claim 1 wherein said at least one respiratory characteristic is a measure of respiration rate.

17. The method of claim 16 wherein at least one setting value is a target respiration rate.

18. The method of claim 17 wherein said measure of respiration rate is an average respiration rate.

19. The method of claim 1 wherein said at least one respiratory characteristic is a measure of arterial partial pressure of carbon dioxide.

20. The method of claim 1 wherein at least one setting value is a target ventilation which is a product of a current target ventilation and the measure of arterial partial pressure of carbon dioxide divided by a desired arterial partial pressure of carbon dioxide.

* * * * *